US007190446B2

United States Patent
Cheng et al.

(10) Patent No.: US 7,190,446 B2
(45) Date of Patent: Mar. 13, 2007

(54) SYSTEM FOR PROCESSING ELECTRONIC DEVICES

(75) Inventors: Chi Wah Cheng, Hong Kong (HK); Hoi Fung Tsang, Hong Kong (HK); Chi Yat Yeung, Hong Kong (HK); Wang Lung Alan Tse, Hong Kong (HK)

(73) Assignee: ASM Assembly Automation Ltd., Hong Kong (HK)

( * ) Notice: Subject to any disclaimer, the term of this patent is extended or adjusted under 35 U.S.C. 154(b) by 396 days.

(21) Appl. No.: 10/741,862

(22) Filed: Dec. 19, 2003

(65) Prior Publication Data

US 2005/0134256 A1 Jun. 23, 2005

(51) Int. Cl.
*G01N 21/00* (2006.01)

(52) U.S. Cl. .................. 356/237.1; 356/237.2

(58) Field of Classification Search ............. None
See application file for complete search history.

(56) References Cited

U.S. PATENT DOCUMENTS

| 5,940,175 A | * | 8/1999 | Sun ............................ 356/237.3 |
| 6,062,084 A | * | 5/2000 | Chang et al. ................... 73/601 |
| 6,614,519 B1 | * | 9/2003 | Latta et al. ............... 356/237.2 |
| 6,813,016 B2 | * | 11/2004 | Quist ....................... 356/237.1 |

* cited by examiner

*Primary Examiner*—Michael P. Stafira
(74) *Attorney, Agent, or Firm*—Ostrolenk, Faber, Gerb & Soffen, LLP

(57) ABSTRACT

A system is provided for processing electronic devices, and in particular for handling, inspecting, sorting and offloading the same. An apparatus for inspecting an electronic device comprises a holder for supporting the electronic device and a driving mechanism for moving the electronic device between an onloading position where the electronic device is placed onto the holder and an offloading position where the electronic device is removed from the holder. A first optical system between the onloading and offloading positions is configured to inspect a first surface of the electronic device while it is supported by the holder, Concurrently or subsequently, a second optical system between the onloading and offloading positions is configured to inspect a second surface of the electronic device that is opposite to the first surface while it is supported by the holder.

18 Claims, 3 Drawing Sheets

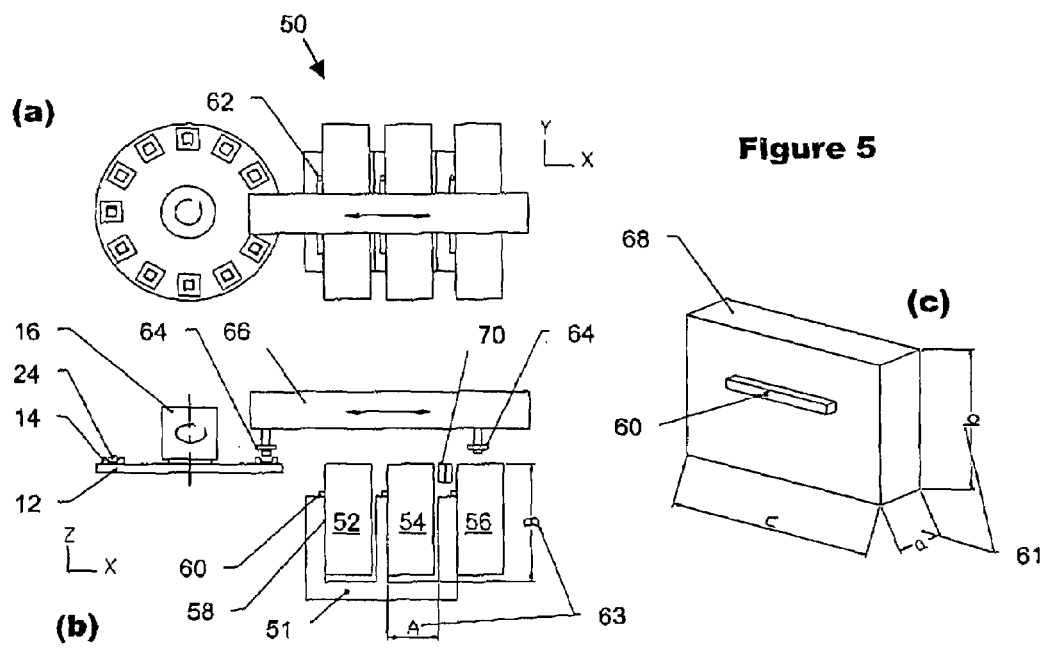
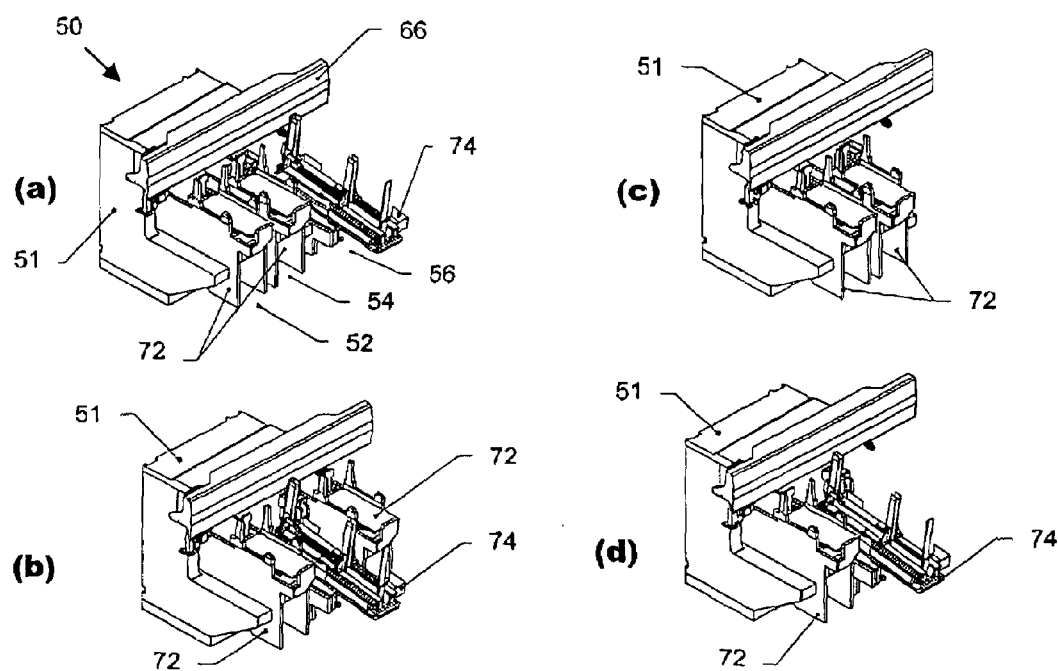

SYSTEM FOR PROCESSING ELECTRONIC DEVICES

FIELD OF THE INVENTION

The invention relates to apparatus and methods for processing electronic devices such as semiconductor packages, and in particular, to the handling, inspection, sorting and offloading of the electronic devices.

BACKGROUND AND PRIOR ART

The sorting of sawn packages on tape is one of the key back-end processes for the manufacture of electronic packages like Chip-Scale Packages ("CSP") when a tape sawing method is adopted. A CSP semiconductor package comprises a lead or ball side for making electrical connections with other devices, as well as a mold side comprising an encapsulant for protecting the internal circuitry. The mold side is also commonly referred to as a marking side as labels or other information may be marked onto this surface of the package. Inspection results on the lead/ball side and mold/marking side is a common criteria used when sorting different packages that have been formed to determine whether packages have been satisfactorily assembled. Therefore, an important performance index for a machine processing CSP packages is its inspection and sorting throughput.

Typically, current sorting systems employ one of two methods. The first method is to align the sawn packages on an adhesive mounting tape with the balls or leads facing away from the tape, and inspect the balls or leads on the packages. The sawn packages are then picked up from the mounting tape with a pick head. Then, the pick head moves to a position where a mold/mark side inspection optics system is positioned to inspect the mold/marked sides of picked packages. After that, good packages are offloaded to a container, such as a tray or tube container, and rejected packages are disposed of in a reject bin. Further, reworked units may be transferred to another tray or bin.

Using this first method, it is difficult to avoid sequential operations involving package alignment on tape, lead or ball side inspection and finally mold or marking side inspection. The result is long cycle time and low throughput. In order to accommodate such operations in sequence, a long traveling distance is common for this method, and therefore the cycle time is further increased. A common way to shorten the cycle time is to provide multiple pick heads (for example, four to ten pick heads) mounted on transfer arms. The drawback of this approach is that the loading and complexity of the arm is increased, and it necessitates a longer conversion time from processing one package size to another as the suction pads of pick heads have to keep changing when the package sizes vary a lot.

The second method involves picking up sawn packages mounted on an adhesive mounting tape using pick heads attached to a turret. Each turret usually comprises more than eight pick heads. The picked packages are placed onto a turntable including holders where ball or lead side inspection will be performed, A second turret with pick heads (again, with usually more than eight pick heads) picks up the packages from the turntable. The mold/mark sides of the picked packages are then inspected at another location along the rotating path of the pick heads of the turret. Thereafter, packages are offloaded to different containers according to quality This second method involves a relatively complex design. Long alignment and machine setup time is incurred as two turrets and one turntable of numerous pick heads have to be aligned. There is also increased conversion time since the many pick heads of the two turrets and holders of the turntable have to be changed if package sizes vary frequently. For the same reason, the conversion kit would be more expensive.

After pick-up, inspection and/or other checking processes, the packages have to be sorted and offloaded to an offloading system. Usually, there are two types of offloading methods, namely offloading to tray and offloading to tube. The good packages are put into trays, tubes or other offloading formats. The reworked packages will usually be put into trays or reworked bins, while the rejected packages are put into reject bins. Usually, for packages of larger sizes (say, 6 mm×6 mm or larger), trays are preferred as the offloading format for good and reworked packages. For smaller packages, (say, 5 mm×5 mm or smaller), the tube offload format is usually preferred for good packages, while the bin format is selected for reworked and rejected packages. Therefore, the offload configuration required may often vary from one user to another and it would be desirable to provide more than one offloading format for a user.

In prior art systems, the configurability of the offloading systems are not flexible enough. Frequently, the offloading configuration has to be determined before the machine is built, and once built, a change of offloading configuration is very difficult if not impossible. As a result, the production lead-time is long.

Furthermore, due to this inflexibility, the offload configuration may only be suitable for one type of packages, For example, a tray-tray-tube configuration may be made to handle large packages such that the third tube offload format is treated as a spare for future use. In case smaller packages that are only suitable for tube offload are used, the offloading cycle time will be longer, since the traveling distance and time is longer and there is no option of repositioning the tube offload nearer to the packages being offloaded.

SUMMARY OF THE INVENTION

It is thus an object of the invention to seek to provide an apparatus and a method of inspecting and handling semiconductor devices that avoids some of the shortcomings of the aforesaid prior art.

It is another object of the invention to seek to provide an improved ejector mechanism for separating electronic devices from an adhesive mounting tape more efficiently.

It is yet another object of the invention to seek to provide a configurable offloading apparatus that is more flexible in use as compared to the prior art.

According to a first aspect of the invention, there is provided an apparatus for inspecting an electronic device comprising: a holder for supporting the electronic device; a driving mechanism for moving the electronic device between an onloading position where the electronic device is placed onto the holder and an offloading position where the electronic device is removed from the holder; a first optical system between the onloading and offloading positions configured to inspect a first surface of the electronic device while it is supported by the holder; and a second optical system between the onloading and offloading positions configured to inspect a second surface of the electronic device that is opposite to the first surface while it is supported by the holder.

According to a second aspect of the invention, there is provided a method for inspecting an electronic device comprising the steps of: supporting the electronic device with a holder; moving the electronic device between an onloading position where the electronic device is placed onto the holder and an offloading position where the electronic device is removed from the holder; inspecting a first surface of the electronic device whilst it is on the holder and being moved from the onloading to the offloading position; and inspecting a second surface of the electronic device that is opposite to the first surface whilst it is on the holder and being moved from the onloading to the offloading position.

According to another aspect of the invention, there is provided an ejection mechanism for separating an electronic device from an adhesive surface of an adhesive tape on which it is mounted, comprising: an ejector pin for pushing and lifting the electronic device in a direction away from the adhesive surface on which it is mounted; an ejector cap operative to support the adhesive tape and electronic device during said pushing and lifting; and a flange at a position where the electronic device is aligned for engagement with the ejector pin for abutting the electronic device and partially lifting it.

According to a further aspect of the invention, there is provided an apparatus for offloading electronic devices for storage, comprising; a plurality of containers in which electronic devices are storable; a platform configured to receive the plurality of containers, wherein each container includes a mechanism for detachably mounting the container to the platform; and a pick-up device for picking up and selectively placing each electronic device into any one of the containers, or to another location.

It will be convenient to hereinafter describe the invention in greater detail by reference to the accompanying drawings which illustrate one embodiment of the invention. The particularity of the drawings and the related description is not to be understood as superseding the generality of the broad identification of the invention as defined by the claims.

BRIEF DESCRIPTION OF THE DRAWINGS

Examples of preferred embodiments of the apparatus and methods in accordance with the invention will now be described with reference to the accompanying drawings, in which:

FIGS. 4A–B illustrate a prior art ejection mechanism to aid in picking up sawn packages from an adhesive tape on which the packages are mounted, whereas FIG. 4C illustrates an ejection mechanism to aid in picking up sawn packages according to a preferred embodiment of the invention, FIGS. 5(a) and 5(b) illustrate a plan view (in the X-Y axes) and a side view (in the X-Z axes) representation respectively of an offloading system according to a preferred embodiment of the invention, which is placed next to an inspection apparatus;

FIG. 5(c) is an isometric view of a generic representation of a offloading sub-system; and FIG. 6(a) to 6(d) show isometric views of examples of different configurations of the offloading system that can be assembled.

DETAILED DESCRIPTION OF THE PREFERRED EMBODIMENTS

Figure 1:
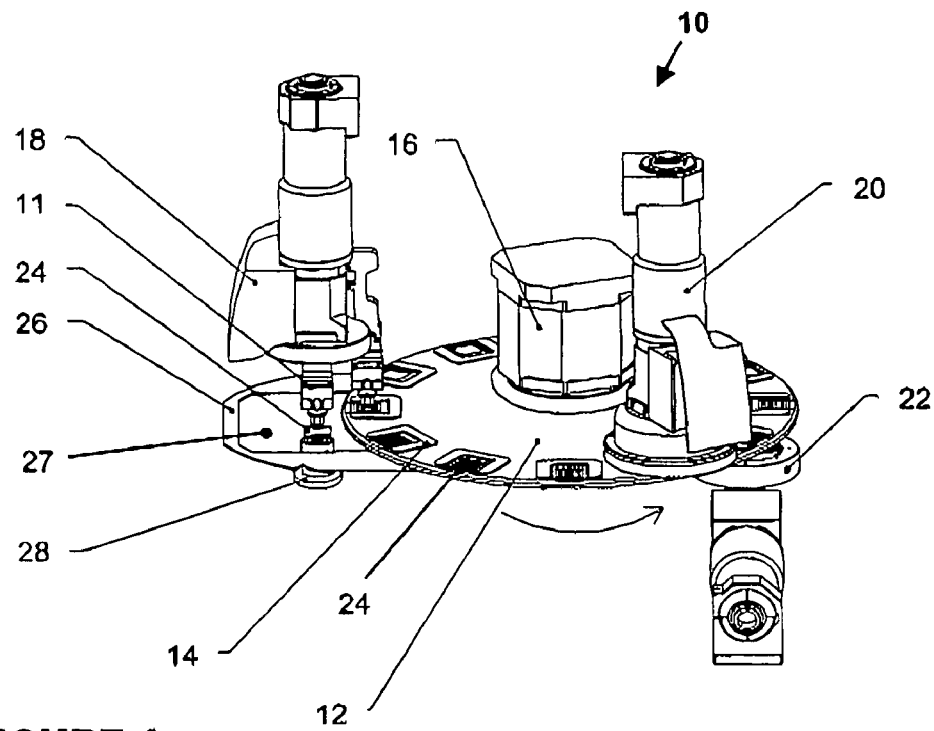
FIG. 1 is an isometric view of an inspection apparatus according to a first preferred embodiment of the invention.
Figure 2:
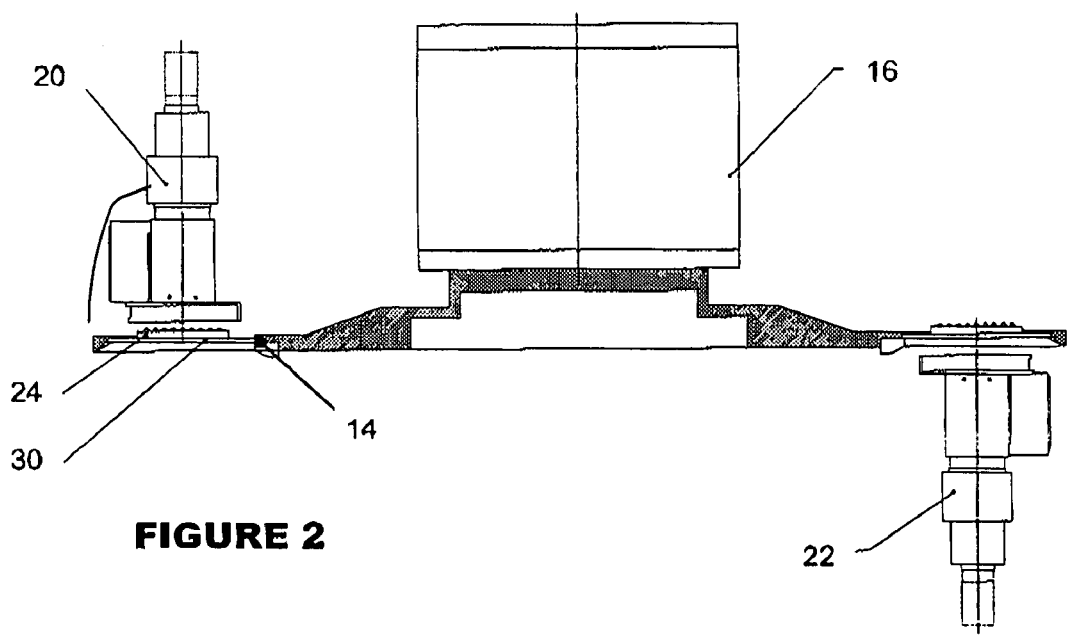
FIG. 2 is a side view of the inspection apparatus of FIG. 1.

FIG. 1 is an isometric view of an inspection apparatus 10 according to a first preferred embodiment of the invention. FIG. 2 is a side view of the inspection apparatus 10 of FIG. 1. The apparatus 10 comprises a pick head 11 (its driving mechanism is not shown), a circular platform or turntable 12 including twelve package holders 14 for holding electronic devices in the form of electrical packages 24, an alignment optical system 18, a first optical system such as top surface (lead/ball) inspection optics 20 and a second optical system such as bottom surface (mold/mark) inspection optics 22. A driving mechanism such as a motor 16 drives the turntable 12 to rotate along. the direction indicated in order to move the packages 24 from an onloading position where they are placed onto the package holders 14 to an offloading position where they are removed from the package holders 14.

The apparatus 10 is characterized by its ability to conduct simultaneous processing of various handling and inspection processes to thereby shorten the processing cycle time. A pick-up device such as a pick head 11 moves between a wafer ring 26 comprising an adhesive mounting tape 27 on which the one or more sawn packages 24 are mounted, and package holders 14 of the turntable 12 at the onloading position. The pattern recognition alignment optical system 18 aligns one or more sawn packages in the X, Y and θ axes with respect to the package holders 14 to ensure correct orientation. The pick head 11 preferably picks up one package 24 from the mounting tape at a time and places it onto a package holder 14 in one segment of the turntable 12 at the onloading position, with the lead/ball side facing up. The turntable 12 in FIG. 1 is divided into twelve segments or holders 14, but the turntable 12 may comprise any suitable number of segments. An ejector pin 28 of an ejection mechanism helps to separate each package 24 from the mounting tape 27 of the wafer ring 26 when it is being picked up by the pick head 11.

The top (lead/ball side) surface of a placed package 24 is inspected by the top surface inspection optics 20 between the onloading and offloading positions and checked for any defect while supported by the package holder 14. The top surface inspection optics 20 is aligned with respect to a package holder 14 in one segment at a position downstream of the placed position of the package 24 along the rotational direction. The bottom (mark/mold side) surface of a placed package 24 is inspected and checked for any defect by the bottom surface inspection optics 22 that is aligned with respect to a package holder 14 in another segment of the turntable 12 at a position downstream and offset from the top surface inspection optics 20 between the onloading and offloading positions along the rotational direction while supported by the package holder 14. However, it is also possible for the top and bottom surface inspection optics 20, 22 to be vertically aligned so as to inspect a package 24 at the same position or segment of the turntable 12.

In order for the bottom surface inspection optics 22 to inspect the bottom surface of a placed package, each package holder 14 preferably comprises a transparent portion. A transparent glass window 30 may accordingly be installed at each package holder 14 to support the package 24 such that the mold/mark surface that is supported on one side of the package holder 14 is visible on an opposite side of the holder 14 underneath the turntable 12.

After completing the inspections, each package 24 is offloaded from its respective holder 14 of the turntable 12 at a further segment downstream along the rotational direction.

It should be appreciated that other types of processing or handling can be arranged whenever space allows, for example, package thickness measurement. The above steps are repeated and the turntable 12 will keep rotating segment by segment so that the simultaneous activities of the various handling, inspection and offloading processes are maintained.

A key feature enabling the mark/bottom side inspection to be conducted as one of the simultaneous processes in the above procedure is thus the glass window installed at the back of the holders 14 on the turntable 12. In fact, such a design feature can be applied to other set-ups of similar apparatus.

Figure 3:
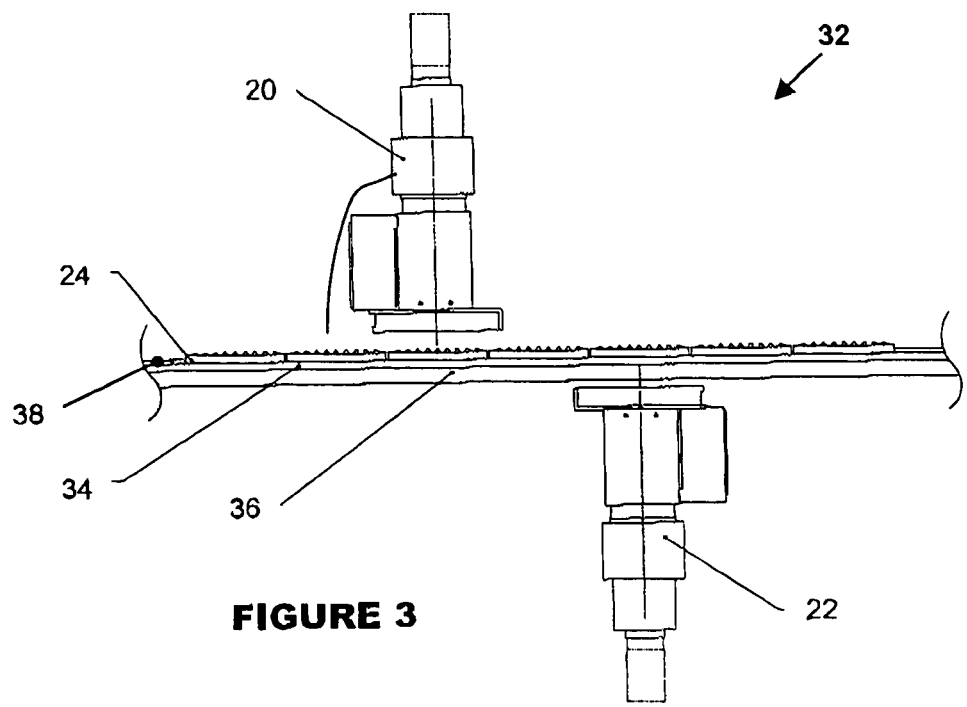
FIG. 3 is a side view of an inspection apparatus according to a second preferred embodiment of the invention.

An example of another type of set-up is a mechanism to move a plurality of packages 24 over a transparent glass support 34, as in FIG. 3. FIG. 3 is a side view of an inspection apparatus 32 according to a second preferred embodiment of the invention. The packages 24 are arranged next to one another on a holder comprising a sliding support 36 and the transparent glass support 34.

As the upstream packages 24 are checked by the top surface inspection optics 20 for top surface (lead/ball) inspection, the downstream packages 24 are checked by the bottom surface inspection optics 22 for bottom surface (mold/mark) inspection through the transparent glass support plate 34. The packages 24 are queued adjacent to one another. A package 24 can therefore be pushed against an adjacent package by a driving mechanism in the form of an indexing device 38 to move the queue of packages 24 together by an incremental distance. The upstream packages checked by the top surface inspection optics 20 will subsequently be checked by the bottom surface inspection optics 22 after moving the required distance. With such a layout, simultaneous processes including concurrent inspection of both sides of packages 24 can be conducted, as in the first embodiment described above.

Figure 4:
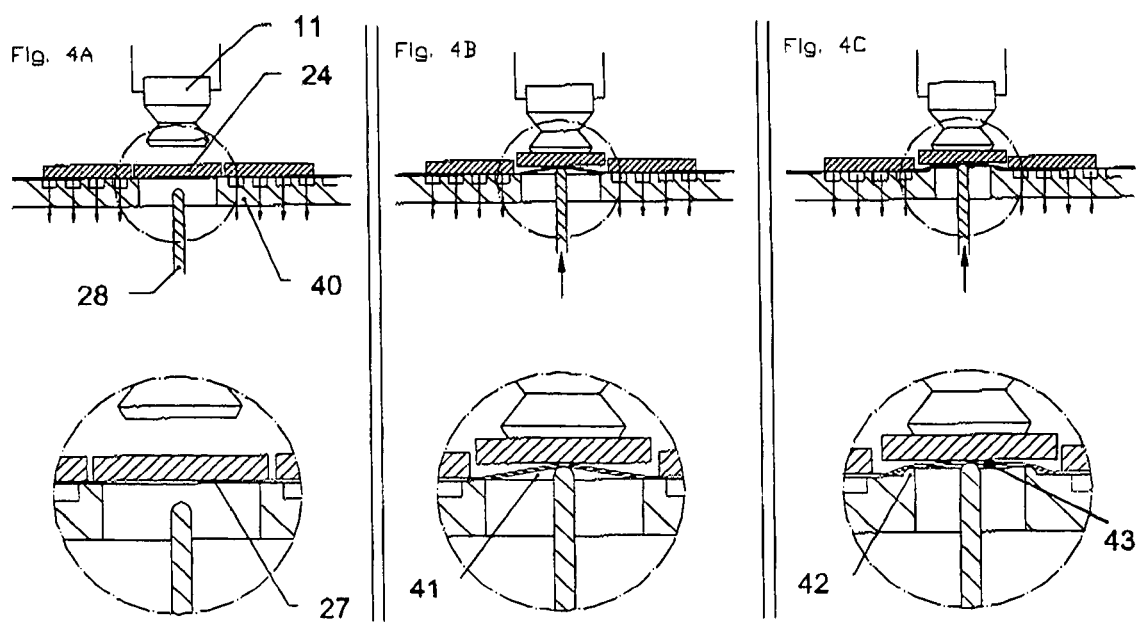

FIGS. 4A–B illustrate a prior art ejection mechanism to aid in picking up sawn packages 24 from an adhesive mounting tape 27 on which the packages are mounted, whereas FIG. 4C illustrates an ejection mechanism to aid in picking up sawn packages 24 according to a preferred embodiment of the invention.

Referring first to FIG. 4A, during ejection of a package 24 mounted on an adhesive mounting tape 27, an ejector cap 40 usually acts as a platform to hold the packages 24, typically by holding the mounting tape 27 with vacuum suction. Then, one of the packages 24 on the mounting tape 27 is moved to the center of the ejector cap 40 into alignment with a position of an ejector pin 28. The package 24 is at stand-by position for pick-up. Referring to FIG. 4B, the ejector pin 28 is then raised to push and lift the mounting tape 27 and with it, the package 24 upwards in a direction away from the adhesive surface so that the package 24 starts to separate from the tape 27. The raising of the mounting tape 27 by the ejector pin 28 forms a pronounced conical shape 41 in the mounting tape 27 during ejection. The rest of the packages 24 on the mounting tape 27 maintain their positions and are still held down by the vacuum force from the ejector cap 40 acting on the mounting tape 27. Simultaneously, a pick head 11 with a vacuum pad is lowered onto the package 24 to pick up the package by vacuum suction. After the package 24 is picked up, the ejector pin 28 returns to its original position. This pickup process is repeated when the next package is indexed to the center of the ejector cap 40.

Referring next to FIG. 4C, the embodiment of the invention includes small steps or flanges 42 on an upper surface of the ejector cap 40 at a position where the package is aligned for engagement with the ejector pin 28. The flange 42 is preferably formed around a perimeter of a hole that the ejector pin 28 passes to engage the package 24. The width of the flanges 42 is preferably a bit smaller than the width of the packages (about two-thirds of the package width) and the height of the flange 42 is preferably a bit smaller than the thickness of the package (about one-third to two-thirds of the package thickness). With the inclusion of the flanges 42, when a package 24 is moved to the center of the ejector cap 40, the flange 42 abuts the package 24 and partially lifts it so that partial separation from the mounting tape 27 is achieved. The ejector pin 28 can then be raised to completely separate the package 24 from the mounting tape 27, and the pick head 11 is lowered onto the package 24 to pick up the package by vacuum suction. As compared to the more pronounced conical shape 41 during ejection using the prior art apparatus (see FIG. 4B), the apparatus according to the described embodiment of the invention produces a relatively flattened conical shape 43 in the mounting tape 27 when it is engaged by the ejector pin 28.

The pre-separation of the package 24 from the mounting tape 27 once it is indexed to the center of the ejector cap 40 can reduce the stroke of the ejector pin 28 required to fully separate the package 24 from the tape 27. Therefore, there is a reduced risk that the ejector pin 28 might penetrate through and damage the tape. This also reduces the likelihood of damaging the back of the package 24. The adhesive mounting tape 27 around the package 24 above the ejector pin 28 is raised less as compared to the prior art. This will reduce the interference to adjacent packages or other objects, such as tie bars near the packages 24. As a result, more stable standby conditions of the adjacent packages and consequently, a higher pick-up yield can be generated.

FIGS. 5(a) and 5(b) illustrate a plan view (in the X-Y axes) and a side view (in the X-Z axes) representation respectively of an offloading system 50 according to a preferred embodiment of the invention. In this description, it is placed next to an inspection apparatus comprising a turntable 12. FIG. 5(c) is an isometric view of a generic representation of a offloading sub-system 68. The offloading system 50 consists of a plurality of offloading slots 52, 54, 56 of similar dimensions and mounting format formed on a multi-slot offloading platform 51. In the described embodiment, there are three offloading slots 52, 54, 56. Each slot 52, 54, 56 can accommodate a container in which the electronic packages are storable, such as a tray 72, tube 74 or other types of offloading sub-systems 68. Therefore, a flexible configuration is possible to achieve various combinations of containers, such as tray-tray, tray-tube, tray-tube-tray and tray-tray-tube. Generally, the tray, tube or other offloading subsystems (e.g., tape and reel) are designed with overall dimensions within the boundary of a slot 52, 54, 56.

It is preferable that the flexible and modular offloading system meet certain criteria. The offloading sub-system such as a tray or tube container, has two important dimensions of width "a" and height "b" (see 61, FIG. 5(c)) which should be less than the two critical dimensions of inner width "A" and allowable height "B" of the offloading slots (see 63, FIG. 5(b)) respectively. The depth "c" of the offloading sub-system (FIG. 5(c)) is not critical as it can extend outside the slot. If they satisfy these criteria, the tray 72, tube 74 or other offloading sub-systems 68 such as tape and reel (not shown) can be placed into any one of the first two slots 52, 54, which allow a maximum width "A" and height "B". The last slot 56 is actually a space next to the outside wall of the second slot 54, and is thus capable of accepting an offload sub-system 68 of a larger size.

Another preferable criterion is that the offloading system 50 should be able to provide universal and standard mounting references (such as by using standard screws to secure the offloading sub-systems) so that various kinds of offloading sub-systems 68 can be detachably mounted into the slots 62, 54, 56 of the offloading platform 51 without tedious modifications.

In use, all the offloading sub-systems 68 may first be mounted by screws (not shown) to the left wall 58 of the slots, and therefore the surface of the left wall 58 of the slot can be used as a reference plane to locate the offloading sub-system 68 in the slot in X-axis. Next, in the Z-axis, a reference block 60 on the left wall 58 of each offload sub-system acts as a mounting reference plane with respect to the upper surface of the left wall 58 of each slot. Third, in the Y-axis, a reference rod 62 is added onto the upper surface of the left wall 58 of each slot and therefore acts as a reference point to locate the reference block 60 and thus the whole offload sub-system 68 in the Y-axis. The surface of the walls 58, reference block 60 and reference rod 62 comprise alignment guides for aligning the offloading sub-systems 68 with the offloading platform 51.

The overall working sequence will now be described. A pick-up device in the form of an offloading pick head 64 picks up packages 24 from the turntable 12. Depending on the inspection results, the offloading pick head 64 selectively places each package 24 into one or other of the offloading sub-systems 68 in an offloading slot 52, 54, 56, or even into a rework/reject bin 70, according to predetermined criteria such that that used for identifying a good or bad package 24. An offloading pick arm 66 with dual offloading pick heads 64 can be used to speed up the pick and place process. When a first offloading pick head 64 moves to pick up a package 24, the other one may move to place a package 24 and vice versa. The turntable 12 will rotate by an equivalent of one segment after each package 24 is picked up so as to move all packages 24 on the turntable 12 by one segment for pick-and-place, inspection and offloading, as discussed with respect to FIG. 1.

However, it is not necessary that the packages 24 are picked up from a turntable 12. In fact, the offloading pick head 64 or other pick-up device may directly pick up packages 24 from a mounting tape 27 or other location to transfer them to the offloading system 50.

FIGS. 6(*a*) to 6(*d*) show isometric views of examples of different configurations of the offloading system 50 that can be assembled. They show offloading configurations comprising tray-tray-tube (FIG. 6(*a*)), tray-tube-tray (FIG. 6(*b*)), tray-tray (FIG. 6(*c*)) and tray-tube (FIG. 6(*d*)). It should be appreciated that other configurations are possible without departing from the principles of the invention.

It should be appreciated that the preferred embodiments described above provide simple apparatus and methods for simultaneous processing of electronic packages, including package pick up, lead/ball inspection, mold/mark inspection, as well as other processes that may be incorporated into the apparatus, as desired.

With these advantages, the said embodiments seek to achieve lower cost, shorter cycle time and higher throughput. Moreover, the simple methods and designs offered by the said embodiments may lead to a more reliable process and higher yield.

The invention described herein is susceptible to variations, modifications and/or additions other than those specifically described and it is to be understood that the invention includes all such variations, modifications and/or additions which fall within the spirit and scope of the above description.

The invention claimed is:

1. An apparatus for inspecting an electronic device comprising:
   a holder for supporting the electronic device;
   a driving mechanism for moving the electronic device between an onloading position where the electronic device is placed onto the holder and an offloading position where the electronic device is removed from the holder;
   a first optical system between the onloading and offloading positions configured to inspect a first surface of the electronic device while it is supported by the holder; and
   a second optical system between the onloading and offloading positions configured to inspect a second surface of the electronic device that is opposite to the first surface while it is supported by the holder,
   wherein the holder includes a transparent portion such that a surface of the electronic device supported on one side of the holder is visible on an opposite side of the holder.

2. The An apparatus as claimed in claim 1, wherein the transparent portion of the holder is made of glass.

3. The apparatus as claimed in claim 1, wherein the holder is formed on a circular platform that is drivable to rotate by the driving mechanism.

4. The apparatus as claimed in claim 3, wherein the platform includes at least one additional holder, the holder and the additional holder each adapted to support one electronic device.

5. The apparatus as claimed in claim 1, including a pick-up device for placing an electronic device on the holder and an alignment optical system for aligning the electronic device with respect to the holder before being picked up by the pick-up device.

6. The apparatus as claimed in claim 1, wherein the first optical system is operable to inspect the electronic device at a first position, and the second optical system is operable to inspect the electronic device at a second position offset from the first position.

7. The apparatus as claimed in claim 1, wherein the first and second optical systems are operable to inspect the electronic device at the same position.

8. The apparatus as claimed in claim 1, wherein the holder is configured to hold a plurality of electronic devices arranged next to one another.

9. The apparatus as claimed in claim 8, wherein the driving mechanism comprises an indexing device operative to move the electronic devices by pushing an electronic device against an adjacent electronic device supported by the holder.

10. A method for inspecting an electronic devices comprising the steps of:
    supporting the electronic device with a holder;
    moving the electronic device between an onloading position where the electronic device is placed onto the holder and an offloading position where the electronic device is removed from the holder;
    inspecting a first surface of the electronic device while the electronic device is on the holder and being moved from the onloading to the offloading position; and inspecting a second surface of the electronic device that is opposite to the first surface while the electronic device is on the holder and being moved from the onloading to the offloading position, wherein the holder includes a transparent portion such that a surface of the electronic device supported on one side of the holder is visible on an opposite side of the holder.

11. The method as claimed in claim 10, wherein the transparent portion of the holder is made of glass.

12. The method as claimed in claim 10, including moving the electronic device and holder on a rotary platform from the onloading position to the offloading position.

13. The method as claimed in claim 12, wherein the rotary platform includes at least one additional holder, the holder and the additional holder each adapted to support one electronic device.

14. The method as claimed in claim 10, including the step of aligning the electronic device with respect to the holder before placing it on the holder.

15. The method as claimed in claim 10, wherein the inspecting of the first surface of the electronic device and the inspecting of the second surface of the electronic device are carried out at positions that are offset from each other.

16. The method as claimed in claim 10, wherein the inspecting the first surface of the electronic device and the inspecting of the second surface of the electronic device are carried out at the same position.

17. The method as claimed in claim 10, including arranging a plurality of the electronic devices next to one another while moving the plurality of electronic devices from the onloading position to the offloading position.

18. The method as claimed in claim 17, including pushing one electronic device of the plurality of electronic devices against an adjacent electronic device of the plurality of electronic devices supported by the holder so as to move the plurality of electronic devices from the onloading position to the offloading position.

* * * * *